United States Patent
Theobald et al.

(10) Patent No.: US 9,089,413 B2
(45) Date of Patent: Jul. 28, 2015

(54) EMERGENCY VASCULAR REPAIR PROSTHESIS

(71) Applicant: Cook Medical Technologies LLC, Bloomington, IN (US)

(72) Inventors: Elizabeth A. Theobald, Bloomington, IN (US); Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/489,047

(22) Filed: Sep. 17, 2014

(65) Prior Publication Data

US 2015/0005872 A1 Jan. 1, 2015

Related U.S. Application Data

(62) Division of application No. 13/106,560, filed on May 12, 2011, now abandoned.

(51) Int. Cl.
*A61F 2/06* (2013.01)
*A61F 2/07* (2013.01)
*A61F 2/82* (2013.01)

(52) U.S. Cl.
CPC . *A61F 2/064* (2013.01); *A61F 2/06* (2013.01); *A61F 2/07* (2013.01); *A61F 2/82* (2013.01); *A61F 2002/826* (2013.01); *A61F 2002/828* (2013.01)

(58) Field of Classification Search
CPC ..... A61F 2/064; A61F 2/07; A61F 2002/826; A61F 2002/828; A61F 2/852; A61B 17/11
See application file for complete search history.

(56) References Cited

U.S. PATENT DOCUMENTS

| | | |
|---|---|---|
| 3,155,095 A | 11/1964 | Brown |
| 4,214,586 A | 7/1980 | Mericle |
| 4,662,884 A | 5/1987 | Stensaas |
| 4,705,039 A | 11/1987 | Sakaguchi et al. |
| 5,064,435 A | 11/1991 | Porter |
| 5,387,235 A | 2/1995 | Chuter |
| 5,720,776 A | 2/1998 | Chuter et al. |
| 6,036,723 A | 3/2000 | Anidjar et al. |
| 6,110,198 A | 8/2000 | Fogarty et al. |
| 6,206,931 B1 | 3/2001 | Cook et al. |
| 6,402,764 B1 | 6/2002 | Hendricksen et al. |
| 6,524,322 B1 * | 2/2003 | Berreklouw ................. 606/153 |
| 7,105,017 B2 | 9/2006 | Kerr |
| 7,112,212 B2 | 9/2006 | Raza |

(Continued)

*Primary Examiner* — David Isabella
*Assistant Examiner* — Suba Ganesan
(74) *Attorney, Agent, or Firm* — Brinks Gilson & Lione (57) ABSTRACT

A prosthesis system for repair of a transected body vessel is provided. The system can include first and second prostheses each including a tubular graft body and a support structure. Each prosthesis can be expandable between a compressed and an expanded configuration. In the expanded configuration, outer surfaces of the first and second prostheses can engage walls of the body vessel. The system can include a sleeve member formable into a tubular body. The first and second prostheses can be coupled to one another at a joint to form a coupled prosthesis. The sleeve member can receive the coupled prosthesis and cover the joint to inhibit leakage therefrom. The prosthesis system can connect first and second portions of the body vessel to permit blood flow therethrough. The sleeve member can be discrete to the coupled prosthesis or can have one end fixedly attached to the coupled prosthesis.

27 Claims, 6 Drawing Sheets

(56) References Cited

U.S. PATENT DOCUMENTS

| | | |
|---|---|---|
| 7,241,300 B2 | 7/2007 | Sharkawy et al. |
| 7,294,147 B2 | 11/2007 | Hartley |
| 7,914,552 B2 | 3/2011 | Shelton, IV |
| 7,914,567 B2 | 3/2011 | Pavcnik et al. |
| 2002/0198587 A1 | 12/2002 | Greenberg et al. |
| 2004/0249399 A1* | 12/2004 | Cinquin et al. ............... 606/153 |
| 2005/0113905 A1 | 5/2005 | Greenberg et al. |
| 2007/0010833 A1 | 1/2007 | Tanaka |
| 2007/0027526 A1 | 2/2007 | Demetriades et al. |
| 2007/0055350 A1 | 3/2007 | Erickson et al. |
| 2008/0082158 A1 | 4/2008 | Tseng et al. |
| 2008/0114466 A1 | 5/2008 | Shelton |
| 2009/0036977 A1 | 2/2009 | Rassat et al. |
| 2009/0112237 A1 | 4/2009 | Paul, Jr. et al. |
| 2010/0069820 A1 | 3/2010 | Zotz |
| 2010/0256741 A1 | 10/2010 | Hansen |
| 2012/0123511 A1 | 5/2012 | Brown |
| 2012/0165915 A1 | 6/2012 | Melsheimer et al. |
| 2012/0232637 A1 | 9/2012 | Demetriades et al. |
| 2012/0271400 A1 | 10/2012 | Lyons et al. |
| 2012/0271402 A1 | 10/2012 | Sargent, Jr. |
| 2012/0330331 A1 | 12/2012 | Paul, Jr. et al. |
| 2013/0018450 A1 | 1/2013 | Hunt |
| 2013/0041451 A1 | 2/2013 | Patterson et al. |
| 2013/0053861 A1 | 2/2013 | Patterson et al. |
| 2014/0088677 A1 | 3/2014 | Bosel |
| 2014/0200650 A1 | 7/2014 | Melsheimer et al. |
| 2014/0324155 A1 | 10/2014 | Paul |

\* cited by examiner

EMERGENCY VASCULAR REPAIR PROSTHESIS

This application claims the benefit under 35 U.S.C. §121 as a division of U.S. patent application Ser. No. 13/106,560, filed May 12, 2011, which is hereby incorporated by reference herein.

BACKGROUND

The present disclosure relates generally to medical devices for emergency repair of body vessels. More particularly, it relates to prosthesis systems used for connecting transected body vessels and gaining hemostasis during open surgical emergency medical procedures.

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include the clamping of the vessel with a hemostat, the use of a balloon tamponade, the ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the trauma physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. With respect to ligation, ligation of the damaged blood vessel may result in muscle necrosis, loss of muscle function, or a potential limb loss or death.

Due to the nature of the body vessel injury that may be encountered, the insertion of shunts or ligation of a blood vessel, for example, often requires that such treatments be rapidly performed at great speed, and with a high degree of physician skill. Such treatments may occupy an undue amount of time and attention of the trauma physician at a time when other pressing issues regarding the patient's treatment require immediate attention. In addition, the level of particularized skill required to address a vascular trauma may exceed that possessed by the typical trauma physician. Particularly, traumatic episodes to the vessel may require the skills of a physician specially trained to address the particular vascular trauma, and to stabilize the patient in the best manner possible under the circumstances of the case.

Some open surgical techniques utilize sutures to affix damaged tissue portions surrounding fittings that have been deployed with the vessel, which requires the trauma physician to take time to tie the sutures properly. Although in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel. Therefore, efforts continue to develop techniques that reduce the physician time required for such techniques, so that this time can be spent on other potentially life-saving measures, and the blood flow is more quickly restored and damage caused by lack of blood flow is minimized.

Trauma physicians generally find it difficult to manipulate a prosthesis for insertion into a body vessel that has been traumatically injured. For example, one difficulty arises from the trauma physician trying to limit the size of the opening created for gaining access to the injured vessel so that such opening requiring healing is as small as possible. Another difficulty is that the injured vessel can be anywhere in the body, having different surrounding environments of bone structure, muscle tissue, blood vessels, and the like, which makes such obstructions difficult to predict in every situation and leaves the trauma physician working with an even further limited access opening. Another potential consideration is the amount of body vessel removed during a transection. The goal would be to remove a portion of the body vessel as small as possible. Yet, a small portion removed from the vessel leaves such a small space between the two vessel portions, thereby making it difficult to introduce the prosthesis between the two vessel portions.

Thus, what is needed is a prosthesis for use in open surgical repair of an injured body vessel, such as an artery or a vein, (and in particular a transected vessel) during emergency surgery. It would be desirable if such prosthesis is easy for a trauma physician to use, and can be rapidly introduced into two vessel portions of a transected vessel, thereby providing a conduit for blood within the injured body vessel.

SUMMARY

Accordingly, a system is provided herein to address at least some of the shortcomings of the prior art. The system can be used to connect two vessel portions such as for open surgical repair of a transected body vessel. In one example, the system can include a first prosthesis and a second prosthesis, each having a first outer end and a second inner end. Each of the prostheses may be discrete and independently moveable between a compressed configuration and an expanded configuration. Each prosthesis can include a substantially tubular graft body and a support structure. A lumen can extend through each prosthesis between the first and second ends thereof. The first end of each of the first and second prostheses, when in the expanded configuration, can engage a respective first or second vessel portion of the body vessel. The second end of at least one of the first and second prostheses can include a coupling member to engage the second end of the other of the first and second prostheses at a joint to form a coupled prosthesis. The coupled prostheses can have a continuous flow path defined by the lumens of the first and second prostheses in communication with one another. The system further can include a sleeve member. The sleeve member can include a tubular body and a passageway extending therethrough to receive the coupled prosthesis. The sleeve member can sealably cover the joint to inhibit leakage therefrom.

In another example, an apparatus can be used to connect first and second vessel portions. The apparatus can include a coupled prosthesis. The coupled prosthesis can include first and second prosthesis portions. Each prosthesis portion can include a substantially tubular graft body attached to a support structure, a first end, a second end, and a lumen extending between the first and second ends. The second end of one of the first and second prosthesis portions can include a coupling member interlocked with the other of the first and second prosthesis portions at a joint to form the coupled prosthesis. Each of the first and second prosthesis portions may be independently movable between a compressed configuration and an expanded configuration. The first end of each of the first and second prosthesis portions may be adapted to engage the first or second vessel portion, respectively. The apparatus can include a sleeve member that can be formable into a substantially tubular body. The sleeve member can have first and second sleeve ends and a passageway extending longitudinally therethrough to receive the coupled prosthesis. The sleeve member can sealably cover the joint to inhibit leakage therefrom.

In yet another example, a method of connecting first and second vessel portions of a body vessel is provided herein. A first end of a first prosthesis in a compressed configuration can be introduced into an end opening of the first vessel portion of the body vessel. A second end of the first prosthesis can remain exposed external to the first vessel portion. The first prosthesis can be expanded to an expanded configuration to engage a vessel wall of the first vessel portion. A first end of a second prosthesis in a compressed configuration can be introduced into an end opening of the second vessel portion of the body vessel. A second end of the second prosthesis can remain exposed external to the second vessel portion. The second prosthesis can be expanded to an expanded configuration to engage a vessel wall of the second vessel portion. The second ends of the first and second prostheses can be coupled to one another at a joint to form a coupled prosthesis. The joint may be positioned external to the first and second vessel portions. The joint of the coupled prosthesis can be covered with a sleeve member to inhibit leakage from the joint.

DETAILED DESCRIPTION OF THE DRAWINGS
AND THE PRESENTLY PREFERRED
EMBODIMENTS

For the purposes of promoting an understanding of the principles of the present disclosure, reference will now be made to the embodiments illustrated in the drawings, and specific language will be used to describe the same. The prosthesis described herein can be useful for repair of a body vessel, such as a blood vessel, during an emergency open surgical procedure. This prosthesis can be particularly useful for repair of a lacerated artery or vein during emergency surgery, and particularly, to obtain hemostasis while maintaining blood perfusion. Other applications for the prosthesis will become readily apparent to one skilled in the art from the detailed description.

Figure 1A:
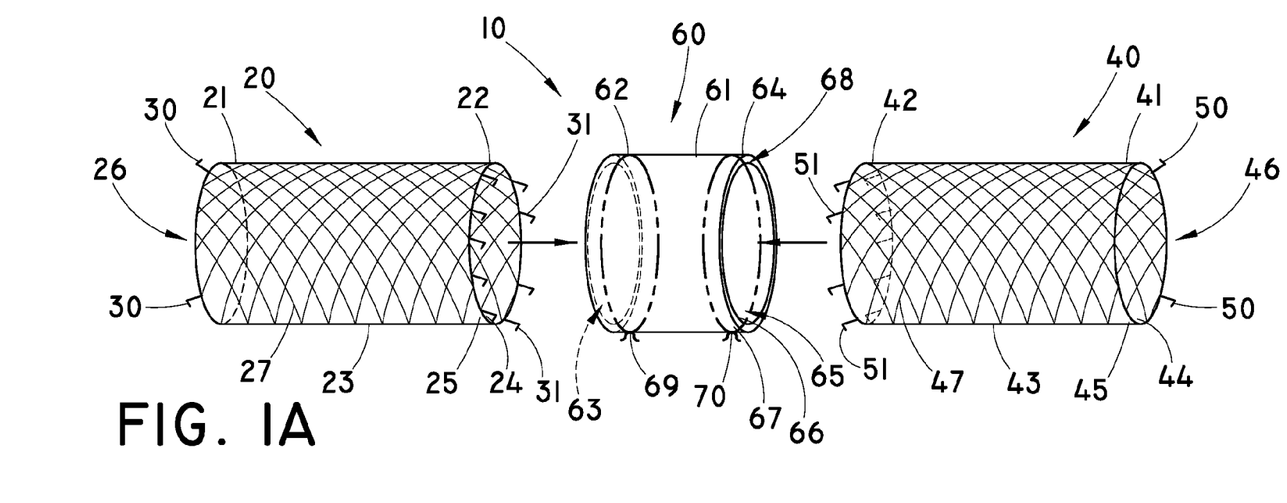
FIGS. 1A-1B are perspective views of one example of a prosthesis system.
Figure 1B:
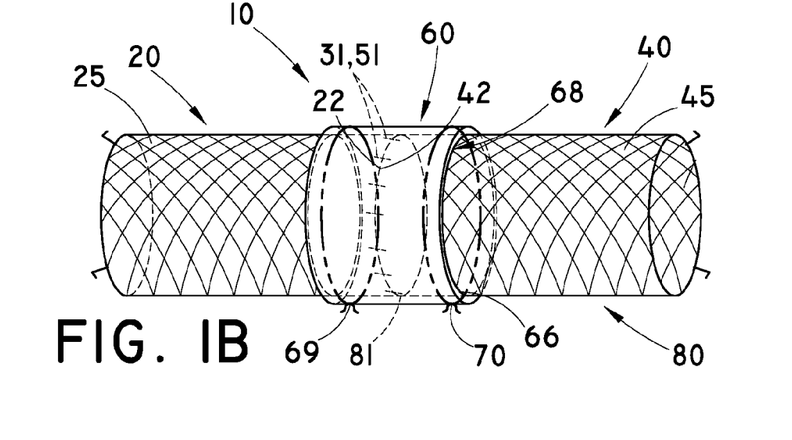

FIGS. 1A-1B depict one embodiment of a prosthesis system 10 having a first prosthesis portion 20, a second prosthesis portion 40, and a sleeve member 60. In some embodiments, the first prosthesis portion 20 and the second prosthesis portion 40 may be identical to one another in all respects. In other embodiments, one prosthesis portion may include features and/or elements that may be distinct from those of the other prosthesis portion. Therefore, the description herein will be confined to the first prosthesis portion 20 except where the features of the second prosthesis portion 40 differ from those of the first prosthesis portion. It will be readily recognized by one skilled in the art that any description of the first prosthesis portion 20 may apply equally to the second prosthesis portion 40 unless such application is inconsistent with this disclosure.

The first prosthesis portion 20 can have an outer first end 21 and an inner second end 22. The first prosthesis portion 20 can include a generally tubular graft body 23 having an inner surface 24 and an outer surface 25. The inner surface 24 of the graft body 23 can define a passageway 26 extending longitudinally within the first prosthesis portion 20. The first prosthesis portion 20 further can include a support structure 27 disposed on the inner surface 24 and/or the outer surface 25 of the graft body 23. At least one anchoring member 30 can be disposed along any portion of the first prosthesis portion 20 between the first end 21 and the second end 22. In one example, the anchoring member 30 can be disposed closer to the first end than the second end, and may be disposed at the first end 21. The anchoring member 30 can be configured to engage an outer wall of a body vessel as further described herein. The anchoring member 30 may include a plurality of anchoring members disposed around the circumference of the prosthesis. The anchoring member 30 can provide vessel fixation, while avoiding adverse conditions associated with disturbing the vasa vasorum and/or pressure induced necrosis of the medium muscular arteries of the type that may result from tying ligatures circumferentially around a connector or a vascular conduit. The anchoring member can include various shaped member structures, including barbs, fibers, bristles, or other protruding and penetrating media, which can be attached to the graft body and/or the support structure, and preferably integral with the support structure.

The first prosthesis portion 20 further can include at least one coupling member 31 disposed along any portion of the first prosthesis portion 20 between the first end 21 and the second end 22. In one example, the coupling member 31 can be disposed closer to the second end than the first end, and may be disposed at the second end 22. The coupling member 31 can engage a segment of the second prosthesis portion 40 as further described herein to securely interlock the two prosthesis portions so that the portions do not detach during blood flow therethrough.

In FIGS. 1A-1B, the second prosthesis portion 40 can have first and second ends 41, 42 and a graft body 43 having an inner surface 44 defining a passageway 46 and an outer surface 45. The support structure 47 can be disposed on the inner surface 44 and/or the outer surface 45 of the graft body 43.

The second prosthesis portion 40 further can include at least one anchoring member 50. The coupling member 31 of the first prosthesis portion 20 can be adapted to attach to the second prosthesis portion 40 itself. Optionally, the coupling member 31 may attach to the support structure 47 of the second prosthesis portion, or may attach to a corresponding coupling member 51 of the second prosthesis portion. Similarly, the coupling member 51 may be included on the second prosthesis portion 40 and adapted to attach to the first prosthesis portion 20. The coupling member 51 can be adapted to attach to the first prosthesis portion 20, for example, by engaging and/or receiving a portion of the first prosthesis portion.

In one example, a portion of the second end of one of the first and second prosthesis portions may have a circumference sized and shaped to slidably receive or to be slidably received within the second end of the other prosthesis portion. The second ends of the prosthesis portions may be frictionally engaged with one another to securely couple the two prosthesis portions. In another example, the coupling member 31 may be configured as a marker band to crimp the first and second prosthesis portions 20, 40 to one another. For example, the marker band may be a tubular member adapted to receive the respective second ends of the first and second prosthesis portions within a lumen extending within the marker band. The marker band may be crimped by any means known in the art to engage the first and second prosthesis portions, thereby securing the prosthesis portions to one another.

Figure 2A:
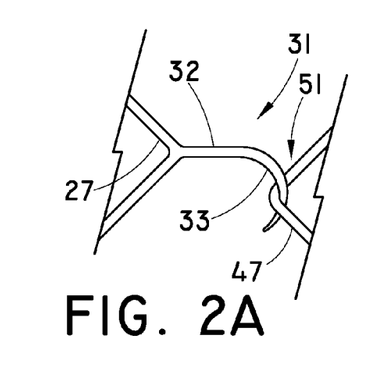
FIGS. 2A-2C illustrate examples of coupling members.
Figure 2B:
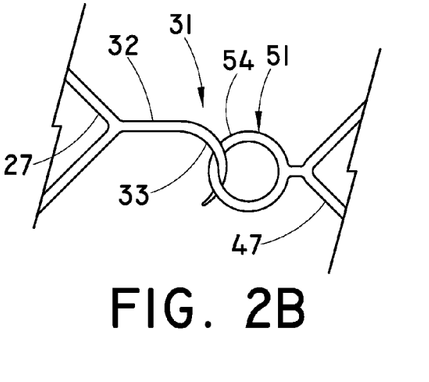
Figure 2C:
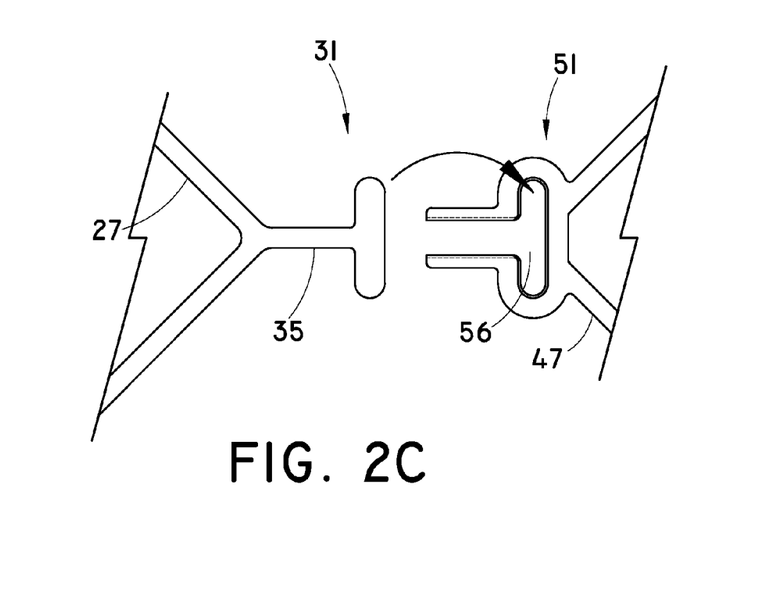

In yet another example, the coupling member 31 may be configured as a hook member or other type of outwardly projecting curved and/or angled member to engage the second prosthesis portion 40. Various examples of projecting members suitable for coupling are illustrated in FIGS. 2A-2C. For example, the coupling member 31 may include a projection 32 extending from the support structure 27 of the first prosthesis portion 20. The projection 32 may terminate in a hook 33 as shown in FIGS. 2A-2B. In FIG. 2A, the support structure 47 of the second prosthesis portion 40, such as an apex formed by two struts, can form the coupling member 51 so that the hook 33 engages the support structure 47 directly. Alternatively, in FIG. 2B, the coupling member 51 of the second prosthesis portion 40 may include an eyelet 54, such as extending from an apex formed by two struts, to receive the hook 33, thereby securing the prosthesis portions to one another. FIG. 2C illustrates an example where the coupling members 31 and 51 are complementary to one another and form a mating relationship. For instance, the outwardly projecting coupling member 31 may include a projecting key member 35, which is shown as a t-member. The key member 35 may engage a keyed slot 56 of the second prosthesis portion 40, which is shaped and sized to receive the t-member so that a mating relationship is formed therebetween. The keyed slot 56 may be formed as part of the support structure 47 of the second prosthesis portion 40 and is configured to receive the key member 35. Other examples of interlocking or mating relationships are contemplated. For example, the coupling member 31 may be configured to threadably engage the second prosthesis portion 40. To this end, the coupling members 31, 51 may be configured as a union type fitting as known in the art. A threaded portion of each of the coupling members may be adapted to threadably engage a union member, thereby securing the prosthesis portions to one another.

Regardless of the specific configuration of the coupling members, engagement between the prosthesis portions may be achieved, for example, by use of an interlocking mechanical member (e.g., a hook, clasp, latch, lock, threaded connector, or other suitable interlocking member) and/or by use of a non-mechanical member (e.g., magnetic clasp or other suitable electro-magnetic member) or adhesives or other bonding agents. Examples of structures that may be suitable for coupling the first and second prosthesis portions to one another are described, for example, in U.S. Pat. No. 7,241,300 to Sharkawy et al.; U.S. Pat. No. 4,705,039 to Sakaguchi et al.; and U.S. Pat. No. 4,214,586 to Mericle; and U.S. Pat. App. Pub. Nos. 2007/0010833 to Tanaka and 2005/0113905 to Greenburg et al., each of which is incorporated by reference herein in its entirety. The coupling members also may be positioned axially inward of the outer end of the respective prosthesis portions such that, when the first and second prosthesis portions are coupled, the distance between the respective bodies of the prosthesis portions may be minimized. A person having ordinary skill in the art will appreciate that the at least one coupling member may be omitted from either the first or second prosthesis portion.

The first and second prosthesis portions 20, 40 can be movable between a radially compressed, or delivery, configuration and a radially expanded, or deployed, configuration. The prosthesis portions may be balloon expandable; however, it is preferred that the prosthesis portions are self-expandable. The first and second prosthesis portions can have a size and shape suitable for at least partial placement within a body vessel, such as an artery or a vein, and most particularly, for placement at the site of a vascular trauma. The first and second prosthesis portions may be easily manipulated during delivery to a transected artery or vein during emergency surgery, and particularly, to obtain hemostasis while maintaining blood perfusion.

The graft bodies 23, 43 of the first and second prosthesis portions can be formed from conventional materials well known in the medical arts. For example, the graft bodies can be formed from an expanded polytetrafluoroethylene (ePTFE), polytetrafluoroethylene, silicone, polyurethane, polyamide (nylon), as well as other flexible biocompatible materials. The graft bodies also can be formed from known fabric graft materials such as woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). The graft bodies also may include a bioremodelable material such as reconstituted or naturally-derived collagenous materials, extracellular matrix material (ECM), submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, and uterine submucosa. One non-limiting example of a suitable remodelable material is SURGISIS® BIODESIGN™ from Cook Medical (Bloomington, Ind.). Another suitable remodelable material is the graft prosthesis material described in U.S. Pat. No. 6,206,931 to Cook et al., which is incorporated herein by reference in its entirety.

The support structures 27, 47 can be configured as stents having any stent pattern known to one skilled in the art. Non-limiting examples of stent patterns include the Z-STENT® and ZILVER® stent, each available from Cook Medical (Bloomington, Ind.). Each support structure can extend along any portion of the respective prosthesis portion. Preferably, the support structure can extend along a length of the respective prosthesis portion between the first and second ends thereof. The support structure can be attached to the graft body of the respective prosthesis portion by sutures sewn therein, wire, staples, clips, bonding agents, or other methods that may be used to achieve a secure attachment to the graft body. The various components of the support structure can be formed from any biocompatible material known in the art. Non-limiting examples of such materials include a biocompatible metal, such as stainless steel (e.g., 316L SS), titanium, tantalum, nitinol or other shape memory materials, or a high-strength polymer.

In FIGS. 1A-1B, the sleeve member 60, formable into a generally tubular body 61, can be coupled to the inner ends of the first and second prosthesis portions 20, 40. To this end, the sleeve member can be formed integrally from a tubular member or can be formed from a planar member that is wrapped and attached to itself, such as sewn with sutures or bonded with an adhesive, in the shape of a tube. The body 61 can have first and second ends 62, 64 having a first end opening 63 and a second end opening 65, respectively. The sleeve member 60 further can have an inner surface 66 and an outer surface 67. The inner surface 66 can define a passageway 68 extending longitudinally within the sleeve member 60. The sleeve member 60 can facilitate the sealing around the joint between the first and second prosthesis portions when coupled to one another to inhibit potential leakage from the joint. The sleeve member also can retain the interlocking engagement of the coupling member(s) and the prosthesis portions.

The sleeve member 60 further can include at least one cinching member coupled to the body 61 for tightening the sleeve member around the first and/or second prosthesis portions 20, 40. The cinching member may be formed of any suitable material known in the art, including, but not limited to, a flexible biocompatible material such as suture material. The cinching member can help maintain a secure engagement between the sleeve member and the coupled first and second prosthesis portions, especially along the joint, to inhibit potential leakage from the joint.

Figure 3:
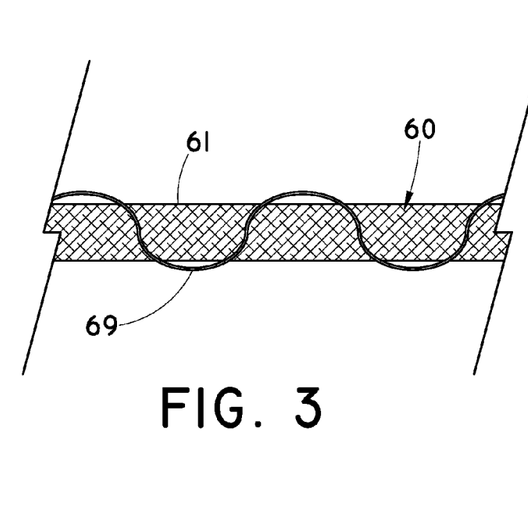
FIG. 3 illustrates a flexible member threaded into a sleeve material of a sleeve member.

FIGS. 1A-1B depict one or more cinching members, such as first and second cinching members 69, 70 disposed, e.g., circumferentially along the first and second ends 62, 64, respectively, of the sleeve member 60. In one example, the cinching members 69, 70 can be configured to surround the outer surface 67 of the sleeve member 60 to sealably cinch the sleeve member 60 along the outer surfaces 25, 45 of the first and second prosthesis portions 20, 40 as further described herein. In FIG. 3, the cinching member 69 can be threaded or woven into the body 61 of the sleeve member 60. The cinching member 70 may be threaded or woven into the body 61 of the sleeve member 60 in similar fashion. Hence, the cinching members can be tightened (e.g., like purse or draw strings) to cinch the first and second ends 62, 64 of the sleeve member 60 by causing the material of the body 61 to bunch up or to fold along the cinching members.

The body 61 of the sleeve member 60 can be formed from conventional materials well known in the medical arts as described herein with reference to the graft bodies 23, 43. The body 61 may be formed from the same or a different material than that used to form the graft body 23 of the first prosthesis portion 20 and/or the graft body 43 of the second prosthesis portion 40. The body 61 can be formed from a material sufficiently flexible so that the sleeve member 60 can be rolled over itself, folded, or otherwise configured to move between a delivery configuration and a deployed configuration as further described herein. The passageway 68 of the sleeve member 60 can be sized and shaped suitably to receive therein the first and/or second prosthesis portions 20, 40 as further described herein.

A coating of one or more therapeutic agents can be included along a portion of the graft bodies, the support structures, and/or the sleeve member. Therapeutic agents for use as biocompatible coatings are well known in the art. Non-limiting examples of suitable bioactive agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, and/or genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the prosthesis system 10 by any suitable method that permits adequate retention of the agent material and the effectiveness thereof for its intended purpose.

FIG. 1B illustrates a coupled prosthesis 80 formed by coupling the first and second prosthesis portions 20, 40 to one another with the coupling member 31 and/or 51 at a joint 81. The first and second prosthesis portions 20, 40 may be arranged in an end-to-end relationship with one another and may be in abutting contact with one another at the joint 81 to form the coupled prosthesis 80. The coupled prosthesis 80 can be received within the passageway 68 of the sleeve member 60. When the first and second prosthesis portions 20, 40 are in the radially expanded, or deployed configurations, the inner surface 66 of the sleeve member 60 can engage the outer surfaces 25, 45 at the inner ends 22, 42 of the first and second prosthesis portions such that an intermediate portion of the sleeve member 60 covers the joint 81 of the coupled prosthesis 80. The cinching members 69, 70 can be tightened to cinch the first and second ends 62, 64 of the sleeve member 60 around the prosthesis portions to inhibit leakage from the joint 81.

Figures 4A, 4B:
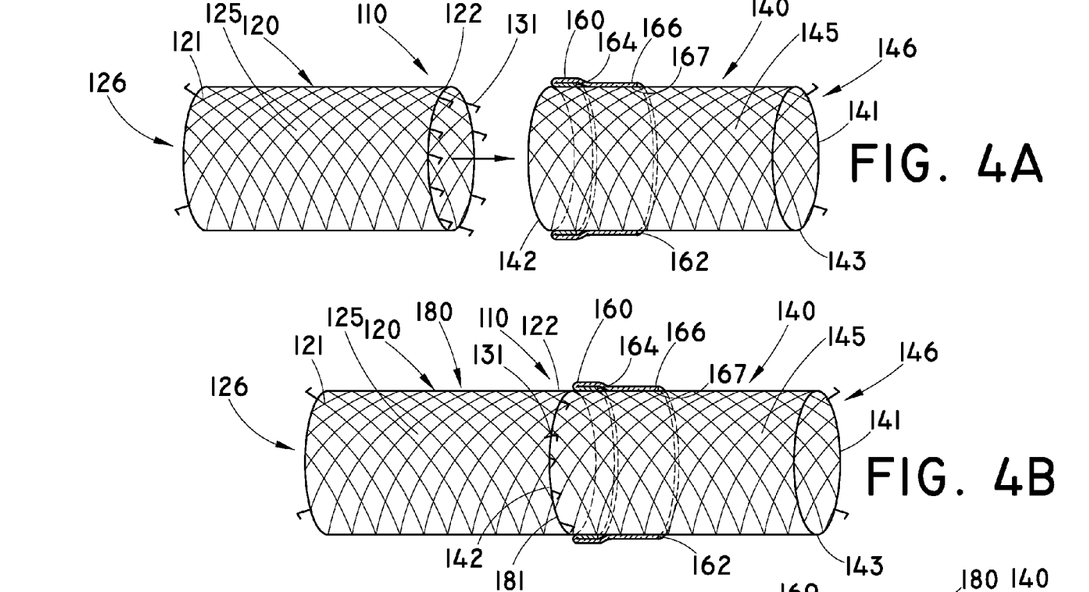
FIGS. 4A-4C are perspective views of another example of a prosthesis system.
Figure 4C:
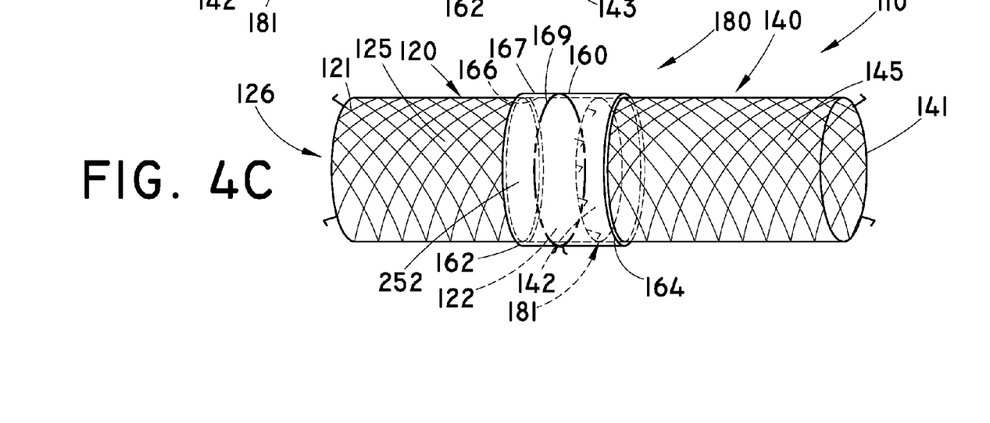

FIGS. 4A-4C depict another embodiment of a prosthesis system 110. In FIG. 4A, the first prosthesis portion 120 with the coupling member 131 is decoupled from the second prosthesis portion 140. One of the ends of the sleeve member 160 can be fixedly attached to one of the prosthesis portions, such as the second prosthesis portion 140, at any point along a length of the prosthesis portion. The other end of the sleeve member 160 may remain free to allow the sleeve member to move between a delivery configuration and a deployed configuration to engage the other prosthesis portion such as the first prosthesis portion 120, as further described herein. For example, a second end 164 of the sleeve member 160 can be fixedly attached to the second prosthesis portion 140. The inner surface 166 of the sleeve member 160 can engage the outer surface 145 of the second prosthesis portion 140 at the second end 142 thereof. The sleeve member 160 can be attached to the second prosthesis portion 140 by any suitable attachment mechanisms such as sutures sewn therein, wire, staples, clips, bonding agents, or other methods that may be used to achieve a secure attachment. In another example, the sleeve member 160 can be an extension of the graft body of one of the prosthesis portions to extend beyond the inner end of the prosthesis portion. In other words, the sleeve material can be formed integrally with the graft body of the prosthesis portion. When the sleeve member is an extension of the graft body, the delivery profile may be reduced in comparison to the configuration with the discretely attached sleeve member.

The sleeve member 160 can be movable between the delivery configuration and the deployed configuration. FIGS. 4A-4B illustrate the prosthesis system 110 with the sleeve member 160 in the delivery configuration. In the delivery configuration, the sleeve member 160 can be disposed away from the inner end 142, e.g., toward the outer end 143 of the second prosthesis portion 140 so that the inner end is exposed for coupling to the coupling member 131 of the first prosthesis portion 120. In other words, the sleeve member 160 may be disposed such that it does not extend beyond the inner end 142 of the second prosthesis portion 140. The sleeve member 160 can be positioned in the delivery configuration by various means such as being rolled back, folded (e.g., like an accordion), scrunched, crumpled, or otherwise configured such that the inner end 142 of the second prosthesis portion 140 can remain uncovered and accessible for coupling between the first prosthesis portion 120 and the second prosthesis portion 140 as described herein. In one example, the sleeve member 160 can be rolled back or everted around the second prosthesis portion 140 as shown in FIGS. 4A-4B so that a portion of the outer surface 167 of the sleeve member is disposed adjacent to and/or in abutting contact with the outer surface 145 of the second prosthesis portion 140.

FIG. 4B depicts the first prosthesis portion 120, with the coupling member 131, coupled to the second prosthesis portion 140 to form the coupled prosthesis 180. The sleeve member may remain in the delivery configuration following coupling.

FIG. 4C illustrates the prosthesis system 110 with the sleeve member 160 in the deployed configuration. In the deployed configuration, an inner surface 166 of the sleeve member 160 can engage the outer surface 125 of the first prosthesis portion 120 and the outer surface 145 of the second prosthesis portion 140 such that the intermediate portion of the sleeve member 160 covers the joint 181 of the coupled prosthesis 180. A first cinching member 169 can be tightened to cinch the first end 162 of the sleeve member 160 around the first prosthesis portion 120 to inhibit leakage from the joint 181. A second cinching member (not shown) also can be included and tightened to cinch another portion such as the second end 164 of the sleeve member 160 further to inhibit leakage from the joint 181.

The embodiment depicted in FIGS. 4A-4C, with the pre-attached sleeve member, can eliminate the need to tighten additional separate cinching members. It is contemplated that various alterations of this or other embodiments may be practiced within the scope of this disclosure. For example, the first end of the sleeve member may be fixedly attached to the first prosthesis portion whereby the second end of the sleeve member may be free to engage the second prosthesis portion. For further example, one end of the sleeve member may be fixedly attached to an intermediate portion of one of the prosthesis portions such that the inner surface of the sleeve member may engage a larger surface area of the outer surface of the first and/or second prosthesis portions. Furthermore, the sleeve member can be attached to the prosthesis portion at a distance away from the end to expose the outer surface of the prosthesis portion for coupling to the other prosthesis portion. The sleeve member may include features configured to assist a clinician in moving the sleeve member from the delivery configuration to the deployed configuration. For example, the sleeve member may include at least one tab member (not shown) extending from the free end 162 of the sleeve member. The tab member may be configured to allow the clinician to grasp the tab member (e.g., by hand or with an instrument such as forceps) to pull the sleeve member from the delivery configuration to the deployed configuration. The tab member thereafter can be removed from the body.

Although the system has been described in connection with its primary intended use for repair of vascular trauma, those skilled in the art will appreciate that the system also may be used to repair other traumatic conditions. Non-limiting examples of such conditions include aneurysms, such as abdominal aorta aneurysms, and surgery for tumor removal.

Figure 5A:
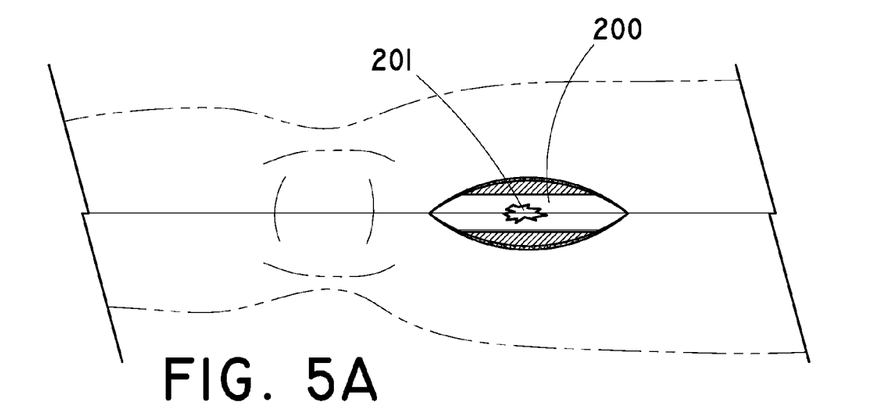
FIGS. 5A-5H illustrate a method of connecting two body vessel portions with one example of a prosthesis system.
Figure 5B:
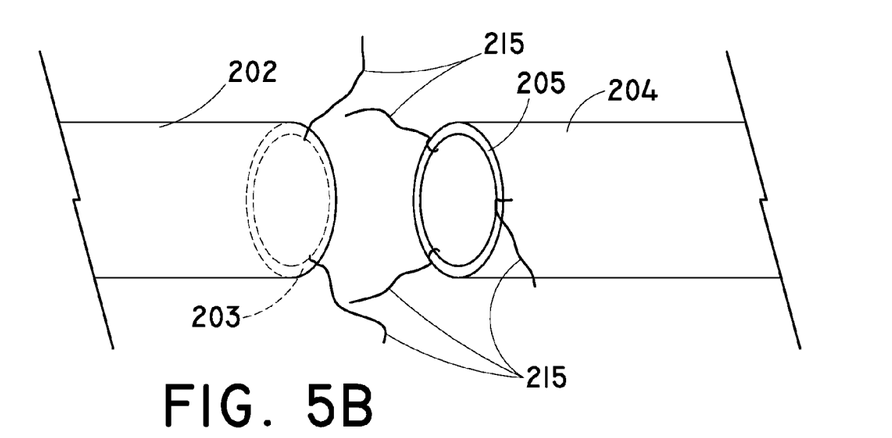

FIGS. 5A-5H illustrate a method of treating a body vessel 200, e.g., during open surgery. The body vessel 200 may be found, for example, in the leg of a patient having been subjected to a traumatic episode resulting in a portion 201 of the body vessel 200 being torn away or otherwise severely damaged, as shown in FIG. 5A. Pre-surgery preparation may be applied to the leg, and a trauma pathway may be formed therein to gain open surgical access to the body vessel 200 and the damaged portion 201 thereof. After clamping the body vessel 200 on both ends of the portion 201 to restrict blood flow temporarily, the body vessel 200 can be cut or transected by the clinician into two portions 202, 204, as shown in FIG. 5B. The transection may be at the damaged portion 201 of the body vessel 200 or as far away as necessary from the damaged portion to remove unhealthy portions of the body vessel or unrepairable portions of the body vessel. Sutures 215 can be attached to end openings 203, 205 of the body vessel portions 202, 204, respectively, to keep them fixed in place and open to facilitate insertion of the prostheses. Forceps also may be used in a similar manner. Any number of sutures 215 can be used to retain the end openings 203, 205 in the open position, although triangulation sutures can be sufficient, with each suture being about 120 degrees apart from the adjacent suture. The first and second prosthesis portions can be selected to have a radial expanded cross-section to fit radially within the body vessel portions 202, 204 and, together, a longitudinal length sufficient to bridge the body vessel portions. To this end, each of the prosthesis portions can be of equal length, or optionally, one of the prosthesis portions can be a different length than the other prosthesis portion so long as the coupled prosthesis is a suitable length to bridge the vessel portions.

Figure 5C:
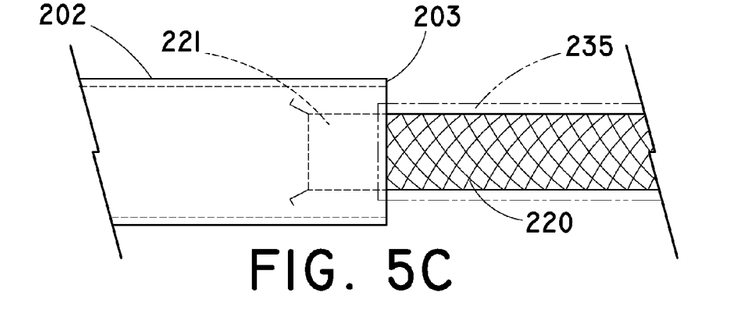

FIG. 5C depicts the first prosthesis portion 220 held in the radially compressed, delivery configuration. The first prosthesis portion 220 can be held in the compressed configuration by any means known in the art. For example, the first prosthesis portion 220 may be held in the radially compressed configuration to be delivered in a retaining member 235 of a delivery system. In one example, the retaining member 235 can be a sheath or introducer, such as described in U.S. Patent Application Publication No. 2008/0082158 to Tseng, which is incorporated herein by reference in its entirety. Other retaining member configurations can be sutures or another filamentary member and/or a sleeve or cuff member disposed upon the first prosthesis portion 220. The first end 221 of the first prosthesis portion 220 can be inserted through the end opening 203 into the vessel portion 202 by a sufficient distance for the purposes of anchoring.

Figure 5D:
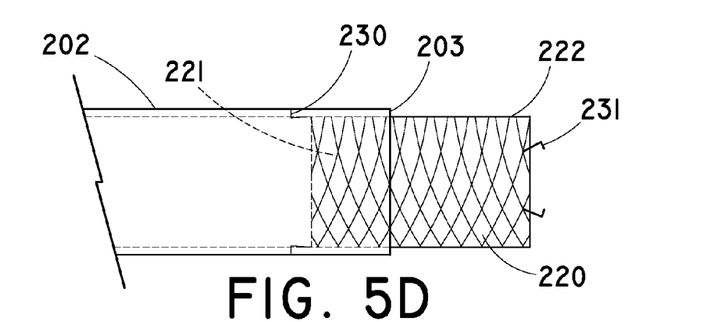

According to FIG. 5D, after insertion, the first prosthesis portion 220 can be permitted to expand from the compressed configuration to the expanded configuration. Such expansion may be initiated by removal or retraction of the retaining member 235. This can permit purchase of the first end 221 of the first prosthesis portion 220 along the wall of the vessel portion 202 as shown in FIG. 5D. Additionally, the anchoring members 230 can engage the wall of the vessel portion 202 to fix the first end 221 of the first prosthesis portion 220 in place relative to the vessel portion 202. The second end 222 of the first prosthesis portion 220 can remain outside of the vessel portion 202 in the space between the vessel portion 202 and the vessel portion 204 for coupling of the first prosthesis portion 220 to the second prosthesis portion 240 as described herein. The second end 222 can have the coupling member 231.

Figure 5E:
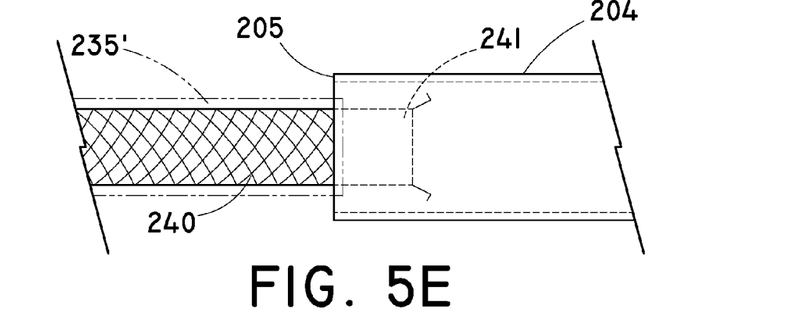
Figure 5F:
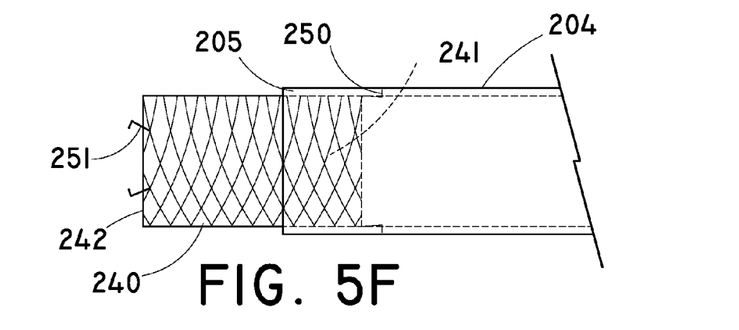

FIG. 5E depicts the second prosthesis portion 240 held in the radially compressed, delivery configuration by a retaining member 235', such as described above with reference to the retaining member 235. The first end 241 of the second prosthesis portion 240 can be inserted through the end opening 205 into the vessel portion 204 by a sufficient distance for the purposes of anchoring. After insertion, the second prosthesis portion 240 can be permitted to expand from the compressed configuration to the expanded configuration. Such expansion may be initiated by removal or retraction of the retaining member 235'. This can permit purchase of the first end 241 of the second prosthesis portion 240 along the wall of the vessel portion 204, as shown in FIG. 5F. Additionally, anchoring members 250 can engage the wall of the vessel portion 204 to fix the first end 241 of the second prosthesis portion 240 in place relative to the vessel portion 204. The second end 242 of the second prosthesis portion 240 can remain outside of the vessel portion 204 in the space between the vessel portion 202 and the vessel portion 204 for coupling of the first prosthesis portion 220 to the second prosthesis portion 240 as described herein. The second end 242 can have the coupling member 251.

Figure 5G:
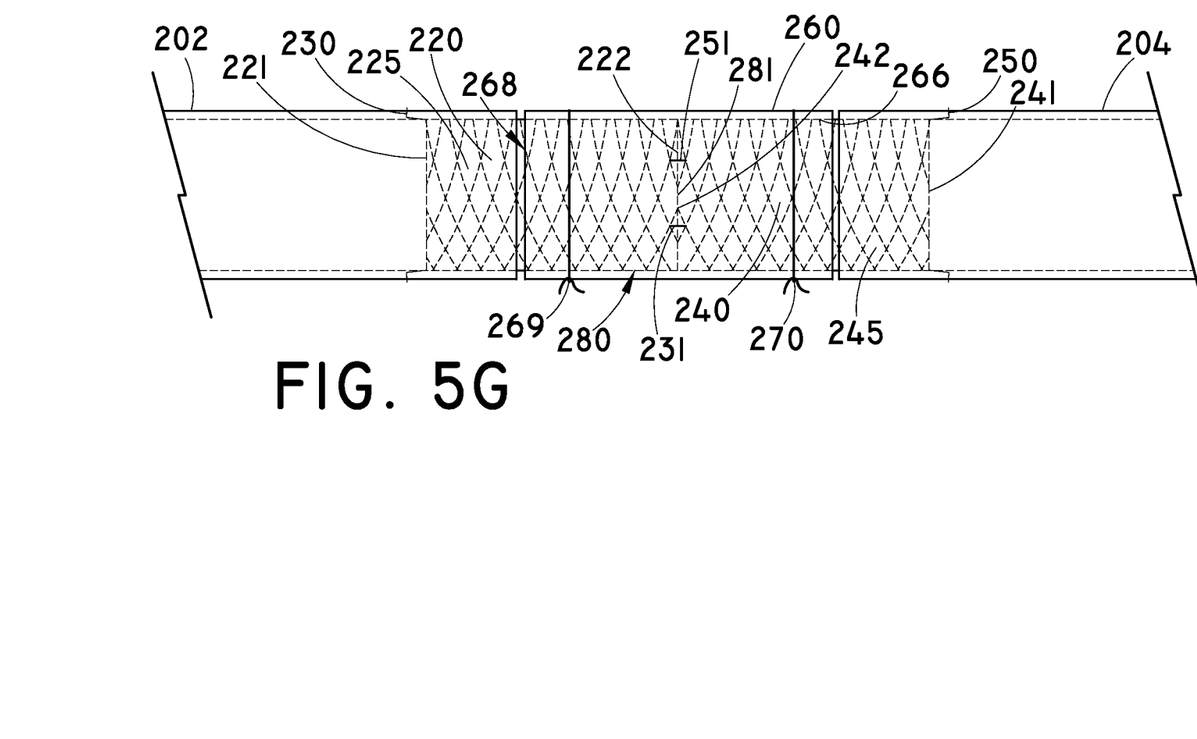

FIG. 5G depicts the first and second prosthesis portions 220, 240 coupled to one another to form the coupled prosthesis 280. Coupling of the prosthesis portions will depend on the structure of the coupling members 231 and/or 251, such as, e.g., shown in FIGS. 2A-2C. In one example, the sleeve member 260 can be inserted over the exposed ends of the prosthesis portions before coupling the prosthesis portions to one another. In this example, the inner ends 222, 242 of the first and second prosthesis portions can be inserted through the opposing end openings of the sleeve member and coupled to one another within the passageway of the sleeve member. Alternatively, the second end of one of the first and second prosthesis portions can be inserted a sufficient length into the sleeve member such that the second end passes completely through the passageway of the sleeve member to protrude from the opposing end of the sleeve member. In this example, both of the second ends of the first and second prosthesis portions can be exposed for more efficient coupling. Once the prosthesis portions have been coupled, the sleeve member can be moved along the outer surface of the coupled prosthesis into position to cover the joint 281 of the coupled prosthesis. In another example, a sheet of sleeve material may be wrapped around the coupled prosthesis portions to form the sleeve member for covering the joint after the coupling of the first and second prosthesis portions. Such an alternative may require sealing a seam extending along the body between the first end and the second end of the sleeve member to inhibit leakage from the seam.

Figure 5H:
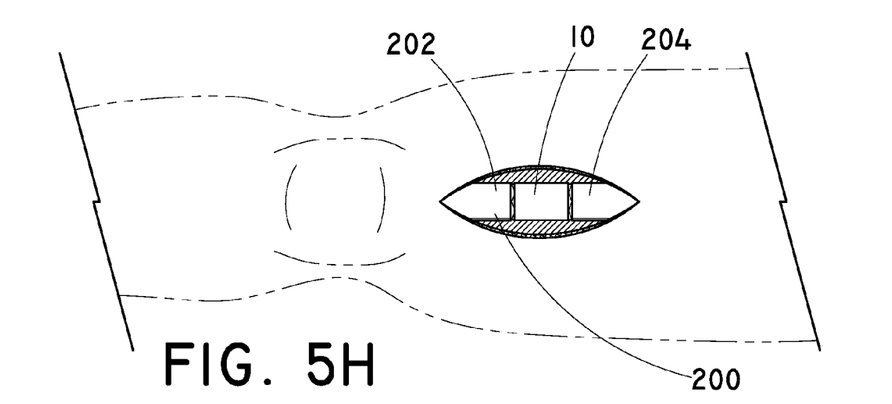

In FIG. 5G, the prosthesis system formed, e.g., by the coupled prosthesis portions, can bridge the first and second portions 202, 204 of the transected body vessel. A conduit for blood flow may be formed by the passageways of the first and second prosthesis portions 220, 240 being in communication with one another and with interior lumens of the first and second vessel portions. The sleeve member can be positioned to be substantially centered over the joint between the coupled prosthesis portions. The cinching member can be tightened to cinch one of the ends or portions of the sleeve member against one of the prosthesis portions. A fluid-tight seal can be formed between the inner surface 266 of the sleeve member and the outer surface 225 and/or 245 of the prosthesis portion to prevent leakage from the joint. When present, a cinching member 269 and/or 270 can be tightened to cinch the other end or another portion of the sleeve member against the other prosthesis portion preferably to form a fluid-tight seal. Portions of the outer surfaces of the first and second prosthesis portions can sealably engage with the luminal walls of the body vessel to inhibit leakage of blood and to force blood to flow throughout the body vessel during emergency surgery, and particularly to obtain hemostasis while maintaining blood perfusion. FIG. 5H shows the prosthesis system deployed and interconnecting the body vessel portions 202, 204 within the leg of the patient. The prosthesis system can be adapted for permanent placement within the patient, thereby obviating a need for subsequent surgical intervention.

Alternatively, when the sleeve member is pre-attached to one of the prosthesis portions, such as shown in FIGS. 4A-4C, the first ends of the first and second prosthesis portions can be inserted into the respective vessel portions 202, 204 as described above with reference to FIGS. 5C-5F. With the sleeve member in the delivery configuration, the ends of the first and second prosthesis portions can be coupled to one another to form the coupled prosthesis. Accordingly, the coupled prosthesis can bridge the first and second portions 202, 204 of the transected body vessel 200. The sleeve member can be moved, such as by unrolling or unfolding, from the delivery configuration to the deployed configuration, such as shown in FIG. 4C. The inner surface of the sleeve member can be placed into contact with the outer surface of the first prosthesis portion. When present, a cinching member can be tightened to cinch the first end of the sleeve member against the first prosthesis portion. A fluid-tight seal can be formed between the inner surface of the sleeve member and the outer surface of the first prosthesis portion to prevent leakage from the joint.

In alternative steps, an adhesive or biosealant 252 may be applied between the sleeve member and circumferentially along an outer surface of the coupled prosthesis, as shown in FIG. 4C. The biosealant can be configured to facilitate attachment between the materials of the sleeve material and the body and support structure of the coupled prosthesis, and may be used instead of the flexible members. It is contemplated that the biosealant can be used in addition to the flexible member. The biosealant may also be configured to seal the joint of the coupled prosthesis to inhibit leakage along the joint. Suitable biosealant materials may include, for example, cyanocrylates and fibrin glue.

It can be appreciated by those skilled in the art that specific features of each embodiment of the system are interchangeable among the various embodiments, even where no references to the specific features are made.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments, and may be combined with each other and/or with currently-known or future-developed technologies while remaining within the scope of the claims presented here. It is therefore intended that the foregoing detailed description be regarded as illustrative rather than limiting. And it should be understood that the following claims, including all equivalents, are intended to define the spirit and scope of this invention.

We claim:

1. An emergency open surgical method of repairing a lacerated or transected blood vessel to obtain hemostasis while maintaining blood perfusion by interconnecting a first vessel portion and a second vessel portion of the lacerated or transected vessel, the method comprising:

gaining open surgical access to the lacerated or transected vessel;

introducing a first end of a first prosthesis in a compressed configuration into the first vessel portion such that a second end of the first prosthesis is exposed external to the first vessel portion;

expanding the first prosthesis to an expanded configuration such that the first end of the first prosthesis engages a wall of the first vessel portion;

introducing a first end of a second prosthesis in a compressed configuration into the second vessel portion such that a second end of the second prosthesis is exposed external to the second vessel portion;

expanding the second prosthesis to an expanded configuration such that the first end of the second prosthesis engages a wall of the second vessel portion;

coupling the second end of each of the first and second prostheses together at a joint external to the first and second vessel portions to form a coupled prosthesis;

covering the joint of the coupled prosthesis with a sleeve member to inhibit leakage from the joint of the coupled prosthesis; and wherein the sleeve member further comprises a first end fixedly attached to one of the first and second prostheses and a second free end, wherein the covering step further comprises moving the second free end of the sleeve member to the other of the first and second prostheses to cover the joint of the coupled prosthesis.

2. The method of claim 1, wherein the second end of at least one of the first and second prostheses further comprises at least one coupling member configured to engage the other of the first and second prostheses.

3. The method of claim 2, wherein the coupling member of one of the first and second prostheses comprises a projecting member configured to interlock with the other of the first and second prostheses.

4. The method of claim 2, wherein the first prosthesis comprises a first coupling member and the second prosthesis comprises a second coupling member, the first and second coupling members configured to interlock with one another to form the coupled prosthesis.

5. The method of claim 1, wherein the first end of each of the first and second prostheses comprises at least one anchoring member to anchor to a vessel wall when in the expanded configuration.

6. The method of claim 1, wherein at least one cinching member is coupled to the sleeve member, and the method further comprises tightening the at least one cinching member to sealably cinch the sleeve member along an outer surface of the coupled prosthesis.

7. The method of claim 6, wherein the at least one cinching member comprises a first cinching member disposed circumferentially along a first portion of the sleeve member and a second cinching member disposed circumferentially along a second portion of the sleeve member, and the method further comprises tightening the first cinching member to sealably cinch the sleeve member along an outer surface of the second end of the first prosthesis and tightening the second cinching member to sealably cinch the sleeve member along an outer surface of the second end of the second prosthesis.

8. The method of claim 6, wherein the at least one cinching member is threaded into the sleeve member.

9. The method of claim 1, wherein the sleeve member further comprises a cinching member disposed at the second free end of the sleeve member, and the method further comprises tightening the cinching member to sealably cinch the sleeve member along an outer surface of the coupled prostheses.

10. The method of claim 1, wherein the first and second prostheses each comprises a tubular graft body and a support structure coupled to the graft body.

11. The method of claim 1, further comprising a sealant disposed between the sleeve member and the outer surface of the coupled prosthesis.

12. The method of claim 1, wherein each of the first and second prostheses is self-expandable.

13. The method of claim 1, wherein an outer surface of the coupled prosthesis is covered by the sleeve member to sealably cover the joint.

14. The method of claim 1, further comprising clamping the blood vessel to temporarily restrict blood flow.

15. The method of claim 1, further comprising transecting the blood vessel into the first and second vessel portions after gaining open surgical access.

16. The method of claim 1, wherein the sleeve member is centered over the joint.

17. The method of claim 1, wherein the sleeve is a sheet wrapped around the coupled prosthesis.

18. The method of claim 1, further comprising attaching sutures to an end opening of each of the first and second vessel portions to keep the end openings fixed in place and open to facilitate insertion of the first and second prostheses.

19. The method of claim 1, wherein the first end of each of the first and second prostheses comprises at least one anchoring member to anchor to a vessel wall when in the expanded configuration, the first and second prostheses each comprises a tubular graft body and a support structure coupled to the graft body, the support structure of each of the first and second prostheses is self-expandable, an outer surface of the coupled prosthesis is covered by the sleeve member to sealably cover the joint, further comprising clamping the blood vessel to temporarily restrict blood flow, and wherein the sleeve member is centered over the joint.

20. An emergency open surgical method of repairing a lacerated or transected blood vessel to obtain hemostasis while maintaining blood perfusion by interconnecting a first vessel portion and a second vessel portion of the lacerated or transected vessel, the method comprising:

gaining open surgical access to the lacerated or transected vessel;

introducing a first end of a first prosthesis in a compressed configuration into the first vessel portion such that a second end of the first prosthesis is exposed external to the first vessel portion;

expanding the first prosthesis to an expanded configuration such that the first end of the first prosthesis engages a wall of the first vessel portion;

introducing a first end of a second prosthesis in a compressed configuration into the second vessel portion such that a second end of the second prosthesis is exposed external to the second vessel portion;

expanding the second prosthesis to an expanded configuration such that the first end of the second prosthesis engages a wall of the second vessel portion;

coupling the second end of each of the first and second prostheses together at a joint external to the first and second vessel portions to form a coupled prosthesis;

covering the joint of the coupled prosthesis with a sleeve member to inhibit leakage from the joint of the coupled prosthesis;

wherein the second end of at least one of the first and second prostheses further comprises at least one coupling member configured to engage the other of the first and second prostheses.

21. The method of claim 20, wherein the coupling member of one of the first and second prostheses comprises a projecting member configured to interlock with the other of the first and second prostheses.

22. The method of claim 20, wherein the first prosthesis comprises a first coupling member and the second prosthesis comprises a second coupling member, the first and second coupling members configured to interlock with one another to form the coupled prosthesis.

23. The method of claim 20, wherein the first end of each of the first and second prostheses comprises at least one anchoring member to anchor to a vessel wall when in the expanded configuration.

24. The method of claim 20, wherein at least one cinching member is coupled to the sleeve member, and the method further comprises tightening the at least one cinching member to sealably cinch the sleeve member along an outer surface of the coupled prosthesis.

25. The method of claim 24, wherein the at least one cinching member comprises a first cinching member disposed circumferentially along a first portion of the sleeve member and a second cinching member disposed circumferentially along a second portion of the sleeve member, and the method further comprises tightening the first cinching member to sealably cinch the sleeve member along an outer surface of the second end of the first prosthesis and tightening the second cinching member to sealably cinch the sleeve member along an outer surface of the second end of the second prosthesis.

26. The method of claim 25, wherein the at least one cinching member is threaded into the sleeve member.

27. An emergency open surgical method of repairing a lacerated or transected blood vessel to obtain hemostasis while maintaining blood perfusion by interconnecting a first vessel portion and a second vessel portion of the lacerated or transected vessel, the method comprising:
   gaining open surgical access to the lacerated or transected vessel;
   introducing a first end of a first prosthesis in a compressed configuration into the first vessel portion such that a second end of the first prosthesis is exposed external to the first vessel portion;
   expanding the first prosthesis to an expanded configuration such that the first end of the first prosthesis engages a wall of the first vessel portion;
   introducing a first end of a second prosthesis in a compressed configuration into the second vessel portion such that a second end of the second prosthesis is exposed external to the second vessel portion;
   expanding the second prosthesis to an expanded configuration such that the first end of the second prosthesis engages a wall of the second vessel portion;
   coupling the second end of each of the first and second prostheses together at a joint external to the first and second vessel portions to form a coupled prosthesis;
   covering the joint of the coupled prosthesis with a sleeve member to inhibit leakage from the joint of the coupled prosthesis;
   wherein the first end of each of the first and second prostheses comprises at least one anchoring member to anchor to a vessel wall when in the expanded configuration, the first and second prostheses each comprises a tubular graft body and a support structure coupled to the graft body, the support structure of each of the first and second prostheses is self-expandable, an outer surface of the coupled prosthesis is covered by the sleeve member to sealably cover the joint, further comprising clamping the blood vessel to temporarily restrict blood flow, and wherein the sleeve member is centered over the joint.

* * * * *